United States Patent [19]
Hamburger et al.

[11] Patent Number: 6,008,729
[45] Date of Patent: Dec. 28, 1999

[54] ALLERGEN DETECTOR SYSTEM AND METHOD

[75] Inventors: Robert N. Hamburger, 9485 La Jolla Shores Dr., La Jolla, Calif. 92037; Ruibo Wang, Goleta, Calif.; Jien-Ping Jiang, Tuscon, Ariz.

[73] Assignee: Robert N. Hamburger, La Jolla, Calif.

[21] Appl. No.: 08/887,533

[22] Filed: Jul. 3, 1997

Related U.S. Application Data

[63] Continuation-in-part of application No. 08/771,641, Dec. 20, 1996, which is a continuation-in-part of application No. 08/679,706, Jul. 11, 1996, Pat. No. 5,646,597.

[51] Int. Cl.⁶ .................................................. G08B 21/00
[52] U.S. Cl. .................. 340/627; 340/630; 250/564; 250/574; 356/438; 116/214
[58] Field of Search ..................... 340/627, 628, 340/630; 250/564, 565, 573, 574; 356/337, 339, 439, 438; 73/28.01, 28.04, 863.21–863.24; 116/214

[56] References Cited

U.S. PATENT DOCUMENTS

| | | | |
|---|---|---|---|
| 3,845,480 | 10/1974 | Steinberg | 340/236 |
| 3,867,640 | 2/1975 | Paulsen | 250/573 |
| 4,175,865 | 11/1979 | Horvath et al. | 340/630 |
| 4,226,533 | 10/1980 | Snowman | 340/630 |
| 4,583,859 | 4/1986 | Hall, II | 356/438 |
| 4,839,529 | 6/1989 | Fruengel | 250/574 |
| 5,001,463 | 3/1991 | Hamburger | 340/627 |
| 5,305,072 | 4/1994 | Sawada et al. | 356/336 |
| 5,383,024 | 1/1995 | Maxey et al. | 356/336 |
| 5,416,580 | 5/1995 | Trainer | 356/336 |
| 5,426,501 | 6/1995 | Hokanson et al. | 356/335 |
| 5,646,597 | 7/1997 | Hambueger et al. | 340/627 |

OTHER PUBLICATIONS

"SIMSLIN II—A Portable Airborne Dust Measuring Instrument Employing a Light Scattering Technique", C. Casswell et al., Conference: Proccedings of the Fourth WVU Conference on Coal Mine Electrotechnology, Aug. 2–4, 1978.

*Primary Examiner*—Daniel J. Wu
*Attorney, Agent, or Firm*—Brown, Martin, Haller & McClain, LLP

[57] ABSTRACT

A light beam is directed from a light source through an air sample so that portions of the beam will be scattered if any particles are present in the path of the beam. A beam blocking device on the opposite side of the air sample is arranged to block all light except light scattered in a predetermined angular range corresponding to a predetermined allergen particle size range. A light focusing lens in front of the light source is arranged to focus the unscattered part of the light beam onto the blocking device. Light transmitted through the blocking device is detected by a light detector and an alarm output signal is produced if the detected amount of light is above a predetermined level. The signal may be used to activate filtering or air conditioning devices.

16 Claims, 2 Drawing Sheets

ALLERGEN DETECTOR SYSTEM AND METHOD

CROSS-REFERENCES TO RELATED APPLICATIONS

This application is a continuation-in-part of application Ser. No. 08/771,641 filed Dec. 20, 1996, which was a continuation-in-part of allowed application Ser. No. 08/679,706 filed Jul. 11, 1996, now U.S. Pat. No. 5,646,597.

BACKGROUND OF THE INVENTION

The present invention is directed to a system and method for detecting airborne allergen particles and for providing an alarm or operating a filtering system if the detected amount of allergen particles is above a predetermined level.

Many individuals suffer from allergies to airborne particles such as dust, pollen and the like which are often present in the environmental air breathed by the individual. The majority of particulates to which many individuals are sensitive are typically in the 5 to 50 micron range. The presence of such particles in air breathed by sensitive or allergic individuals may give rise to symptoms such as asthma, coughing, sneezing, as well as skin rashes and anaphylaxis. Knowledge or warning of the presence of high levels of allergenic particles in the environmental air is helpful to such individuals, potentially enabling them to take medication, leave the area, or activate allergen removing filters, before the onset of serious symptoms.

In U.S. Pat. No. 5,001,463 of Hamburger an allergen particulate detecting apparatus is described in which air is blown through a passageway in which an allergen particle sensor is mounted for trapping allergen-sized particles. The output signal of the sensor is dependent on the amount of trapped particles, and an alarm is activated if the signal is above a predetermined level.

SUMMARY OF THE INVENTION

It is an object of the present invention to provide a new and improved allergen detection system and method.

According to one aspect of the present invention, an allergen particle detection system is provided which comprises a light source for directing a light beam through a sample of environmental air, a beam blocking assembly positioned in the light path on the opposite side of the air sample for blocking transmission of all light except the portion of light scattered in a predetermined angular range corresponding to a predetermined allergen particle size range of 0.5 micron to 500 microns, a focusing lens positioned in front of the light source for focusing the light beam onto the beam blocking device, a detector positioned to receive light transmitted through the beam blocking assembly, and a control circuit connected to the detector for generating an alarm output signal if the detector output is above a predetermined level.

The alarm output signal may be used to activate an audible or visual alarm device, or to turn on a filtration and ventilation system including HEPA or allergen particle filters. The filtration system may be turned off as soon as the detected allergen particles have returned to a safe level. The apparatus may be relatively small, and may be conveniently designed for wall mounting.

The beam blocking assembly preferably comprises a disc of light blocking material centered on the optical axis and of predetermined diameter to block all unscattered light and light scattered at angles below a predetermined minimum angle which is scattered by particles larger than the largest allergen particle size, and an annular ring of light blocking material having an inner diameter corresponding to the predetermined maximum scattering angle, such that light scattered at angles larger than the maximum scattering angle is blocked. The focusing lens is arranged to focus the light beam onto the central, beam blocking disc.

In a preferred embodiment of the invention, the light source is a light emitting diode (LED). By focusing the output beam of the LED onto the beam blocking disc, the need to collimate the beam is avoided. Since an LED has a more diffuse emitting region than other lasers, it is more difficult to collimate, requiring a complex optical arrangement. The focusing lens and beam blocker arrangement allow an inexpensive LED to be used as the light source, without requiring any complex collimator arrangement. The diameter of the beam blocker disc is sufficient to block all unscattered light from the LED. In other words, it has a diameter slightly larger than the focused spot diameter of the focusing lens. If no allergen-size particles are present, all light will be blocked by the beam blocker.

In a preferred embodiment, the dimensions of the blocking assembly were arranged to block all light except that scattered by particles in the size range of 5 microns to 50 microns, although a size range of up to 0.5 to 500 microns may alternatively be used.

In another embodiment of the invention, a two-part beam blocking assembly may be provided, comprising a first beam blocking device having a circle of light blocking material of predetermined diameter for blocking at least the unscattered portion of the light transmitted through the air sample, and a second beam blocking device having at least one pinhole for transmitting light in the predetermined angular range. Preferably, the blocking circle in the first device is dimensioned to block unscattered light and light scattered at angles below the minimum angle in the predetermined range. The second device preferably has one aperture centered on the optical axis with a diameter such that light scattered at angles above the maximum angle in the range is blocked.

Preferably, the control circuit for generating the alarm output signal includes a pulse counter for counting the number of allergen particles detected in a certain time period. The pulse generator is arranged to trigger an alarm indicator if the number of counts in the selected time period is above a predetermined trigger value. Preferably, the trigger level is adjustable, so that the user may select the sensitivity level.

According to another aspect of the present invention, a method of detecting allergen particles in the air is provided which comprises the steps of directing a light beam through a sample of environmental air so that light will be scattered by any particles in the air, focusing the light beam onto a blocking member on the opposite side of the air sample which has a size greater than of the focused light beam, blocking light scattered outside a predetermined angle range on the opposite side of the air sample, transmitting only scattered light within the predetermined range of scattering angle, detecting the transmitted light and producing a first output signal at a level proportional to the amount of light transmitted, and generating an alarm output signal if the first output signal is above a predetermined level.

This system and method readily discriminates between allergen-size particles in the 5 to 50 micron range and larger, non-allergenic particles so as to produce an accurate indication of the allergen particle levels in a room or enclosed area. Preferably, the level at which the alarm signal is produced is adjustable. The apparatus can be readily connected to turn on auxiliary air cleaning appliances or filters such as HEPA filters.

BRIEF DESCRIPTION OF THE DRAWINGS

The present invention will be better understood from the following detailed description of some preferred embodiments of the invention, taken in conjunction with the accompanying drawings, in which like reference numerals refer to like parts, and in which.

DESCRIPTION OF THE PREFERRED EMBODIMENTS

Figure 1:
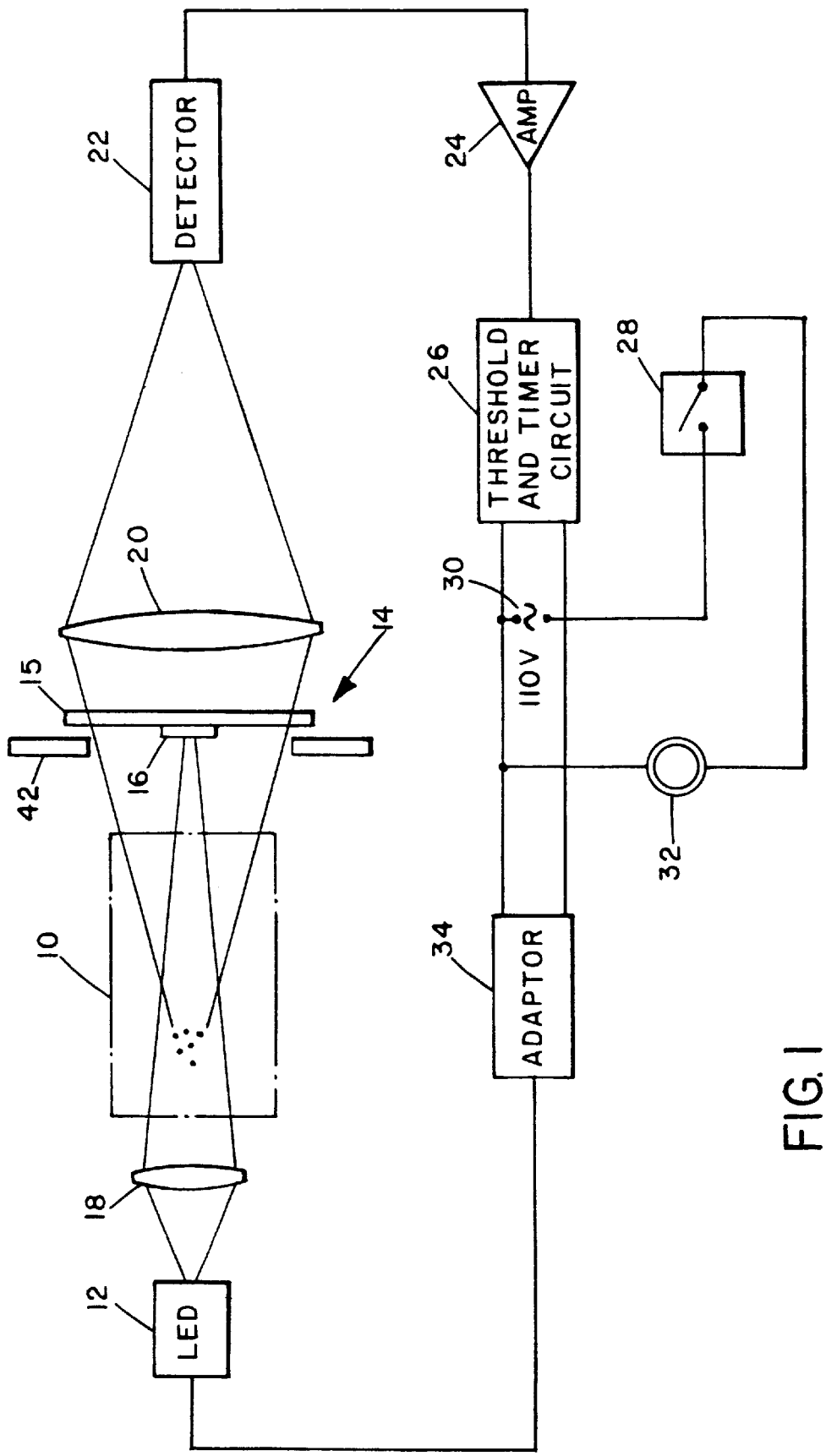
FIG. 1 is a block diagram of an allergen particle detector apparatus according to a first embodiment of the invention.

FIG. 1 of the drawings illustrates an allergen particle detector apparatus according to a first embodiment of the present invention. The apparatus will be enclosed in a suitable outer housing shaped to provide a passageway or air gap 10 for exposure to environmental air in order to test an air sample for allergen-size particles, as in our co-pending application Ser. No. 08/771,641 referred to above, the contents of which are incorporated herein by reference. A laser beam is directed from laser diode or LED 12 across the air sample 10 towards a beam blocking device 14 on the opposite side of the air gap. The device 14 comprises a transparent circular flat glass plate 15 with an opaque portion or disc 16 at the center of the plate. Portion 16 may be produced by black paint, or a black plastic or metal insert at the center of the plate. A focusing lens 18 in front of LED 12 is arranged to focus the laser output beam onto the beam blocking disc 16. The actual dimensions of the opaque blocking portion will be dependent on the cross-sectional shape and dimensions of the focused output beam of laser diode 12, and the particle size range to be detected by the apparatus. The LED may emit infrared light (0.8–1.0 micron) or visible light. In one embodiment of the invention an LED emitting at the wavelength of 670 nm. was used.

The majority of allergen particles to which individuals may be sensitive are in the size range of 5 to 50 microns, although a small quantity of allergen particles may be found at sizes from 0.5 to 5 microns and from 50 to 500 microns. Thus, substantially all allergen particles will be found in the size range of 0.5 to 500 microns, with the maximum number being in the range of 5 to 50 microns. Therefore, the apparatus is preferably designed to detect particles in the size range of 0.5 to 500 microns, although it may alternatively be designed to detect particles in the range of 5 to 50 microns, since the majority of allergens will be in this size range.

The angle at which light is scattered by a particle will be dependent on the wavelength of the light and the size of the particle. Airborne particles of different sizes have quite different light scattering properties. Larger particles will scatter light at smaller angles. For a red to infrared light source in the wavelength range of 0.6 micron to 1.0 micron, the smallest scattering angle for a particle size range of 0.5 to 50 microns is about 4° to 5° (see *Electromagnetic Scattering*, R. L. Rowell and R. S. Stein, ed., p. 140, Gordon and Breach 1965). If the blocking device is at a distance of L from the air sample, the radius of the central blocking portion should be L*tan(5°), in order to block light scattered at angles less than 5°, i.e. light scattered by particles larger than 50 microns. The blocking device can therefore be arranged to block all light scattered by particles of size greater than 50 microns.

Lens 20 is positioned behind blocking device 14 in order to focus light transmitted by the device 14 onto a detector 22. The output of detector 22 is connected via amplifier 24 to a threshold and timer circuit 26. If the output of detector 22 is above a predetermined threshold, relay switch 28 is closed to connect power supply 30 to the air filter 32, which may be any suitable HEPA filter. The power supply is also connected via adapter 34 to the laser diode.

The beam blocking device 14 also includes an annular ring 42 of light blocking material is placed in front of disc 15. Alternatively, the disc itself may be painted black around a corresponding annular area. An annular ring through which light will be transmitted is defined between beam blocking disc 16 and annular ring 42. The light transmitting annular ring will have a predetermined inner diameter d1 corresponding to the diameter of the center disc 16, and a predetermined outer diameter d2 corresponding to the inner diameter of ring 42. The dimensions d1 and d2 will be determined based on the particle size range to be detected. The majority of allergen particles are in the size range of 0.5 to 50 microns. These will scatter light in the range of around 5° to 27°, as described above in connection with the first embodiment. The diameter d1 is therefore determined from the relationship L*tan(5°). The diameter d2 is determined from L*tan(27°), where L is the distance of the discriminator 118 from the sensitive region or air sample. With these dimensions, the device 118 will transmit only light scattered in the range of 5° to 27° by particles in the range from 0.5 to 50 microns. The dimensions can be varied dependent on the desired particle size range to be detected, which may be expanded to 0.5 to 500 microns if desired, although the majority of allergen particles are found in the range from 0.5 to 50 microns.

The use of the focusing lens 18 in conjunction with blocking disc 16 allows a simple and inexpensive laser light emitting diode or LED 12 to be used as the light source, instead of other, more expensive types of laser emitters. The focusing lens avoids the need to use a complex collimating arrangement for collimating the diffuse output beam of LED 12.

Figure 2:
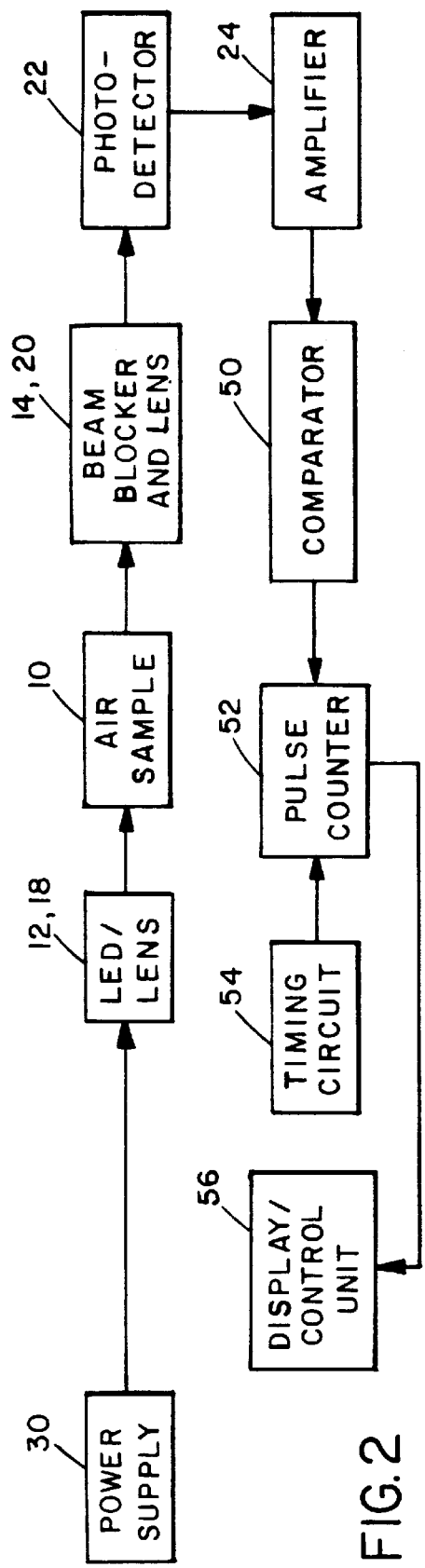
FIG. 2 is a block diagram illustrating a modified output control circuit.

FIG. 2 illustrates a modified output circuit for the allergen detector system, which provides greater sensitivity in situations where the actual number of allergens present in the air is low. Apart from the modified output circuit, the detector apparatus is otherwise identical to that of FIG. 1, and like reference numerals are used for like parts as appropriate.

The sample area or air gap 10 is of relatively small volume, of the order of a few cubic centimeters. When the allergen density in the air is low, allergen particles will pass through the sensitive region of the allergen detector apparatus only intermittently. Thus, the detector will register counts only in a discrete manner. In the circuit as illustrated in FIG. 2, signal pulses from detector 22 are connected to amplifier 24. The amplified pulse output is connected to comparator 50 to make a regulated pulse. The pulse output of comparator 50 is counted by pulse counter 52. A timing circuit 54 resets the pulse counter at predetermined intervals, for example every 30 seconds. Whenever there is an allergen particle in air gap 10, the scattered light will trigger the photodetector and subsequently the amplifier and comparator will produce an output pulse. This pulse represents detection of a single allergen particle.

The pulse counter 52 registers all pulses in a certain period of time, determined by timing circuit 54. The total number of pulses registered is displayed on light emitting diode display unit 56. After each measurement period, say 30 seconds, the counter is reset to zero counts and begins to accumulate counts again. The counter trigger level is preferably adjustable by the user, so that different sensitivity levels can be detected as desired by the user.

This arrangement permits measurement of allergen density in a low range, and is particularly useful with a stand-alone allergen detector unit, where no additional air moving apparatus is used. With such an arrangement, allergen particles will drift randomly into the air gap, and there may be periods during which no allergen particles are detected when the allergen density in the air is low. By accumulating particle counts over an extended period of time, lower allergen particle density levels may be detected. Any standard, off-the-shelf pulse counter may be used, such as a 7492 counter.

Figure 3:
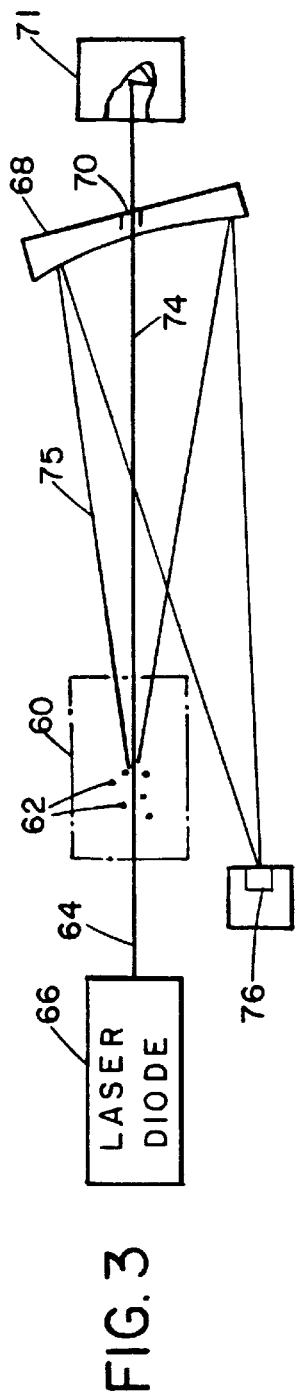
FIG. 3 is a block diagram of an allergen particle detector according to a second embodiment of the invention.

FIG. 3 of the drawings illustrates a modified allergen detector apparatus according to a second embodiment of the invention. As before, the apparatus will be enclosed in a suitable housing (not illustrated) shaped to provide a passageway or air gap 60 for exposure to environmental air, in order to test an air sample within air gap 60 to detect the presence of allergen-size particles 62, as described in application Ser. No. 08/771,641 referred to above.

A laser beam 64 is directed from laser diode 66 through the air sample in gap 60. A reflecting concave mirror 68 with a central opening 70 of predetermined dimensions is positioned on the opposite side of air gap 60. A lens 18 (not illustrated) may be positioned between diode 66 and air gap 60 as in the previous embodiment in order to focus the laser output beam onto central opening 70 in the concave mirror, which acts in the same way as the beam blocking disc of the previous embodiment. The actual dimensions of the central opening 70 will be dependent on the cross-sectional shape and dimensions of the focused laser beam and the particle size range to be detected by the apparatus, as in the previous embodiment.

Figure 4:
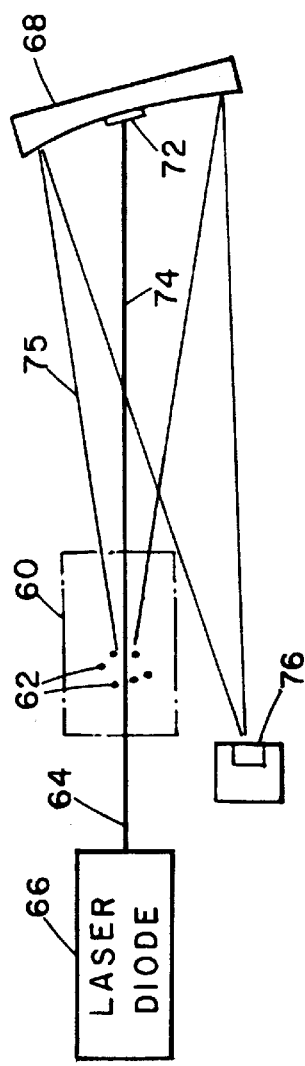
FIG. 4 is a block diagram similar to FIG. 3 illustrating a modification.

FIG. 4 illustrates a modification which is similar to the embodiment of FIG. 3 with the exception that the central opening 70 in concave mirror 68 is replaced by a black beam blocker 72 which may be provided by black paint or a black disc applied to the mirror. All other parts of the embodiment of FIG. 4 are identical to that of FIG. 3, and like reference numerals have been used for like parts, as appropriate.

In both FIG. 3 and FIG. 4, the unscattered light beam 74 is eliminated, either by leaking through the central opening 70 in the mirror in FIG. 3 to a beam dump 71, or by blocking it with beam blocker 72 at the center of the mirror, as in FIG. 4. In both cases, allergen particles in the air gap 60 will scatter the light beam, and the scattered light beam 75 will be reflected from the mirror 68 onto a photodetector 76 placed alongside the laser diode. The size of the central opening or beam blocker is preferably sufficient to block or receive unscattered portions of the light beam and portions scattered at angles below a predetermined minimum angle as described above in connection with the preceding embodiments, while the outer diameter of the mirror may be selected such that light scattered above a predetermined maximum angle passes the mirror without reflection. Thus, only light scattered in the desired angular range corresponding to allergen-size particles will be redirected along the light path to the detector 76.

Operation of the apparatus of FIGS. 3 and 4 is otherwise identical to that of the first embodiment as described above in connection with FIGS. 1 and 2, and similar output circuitry will be provided for measuring the output of detector 76. However, this embodiment has the advantage that the apparatus will be more compact, since the light path is doubled back, shortening the overall length of the apparatus.

The allergen particle detector of this invention detects only allergen-size particles and eliminates light scattered by particles of sizes outside the allergen size range of 0.5 to 50 microns. The light source is a simple and inexpensive laser light emitting diode, used with a focusing lens to focus the unscattered beam onto a beam blocking disc. The allergen detection level may be readily adjusted by the user. The apparatus is easy and inexpensive to manufacture, and simple to operate. It provides real time, accurate detection of excessive levels of allergen particles in the air, providing a warning to sensitive individuals who may need medication and also allowing allergen filtering equipment to be activated under such conditions to clean the air.

Although preferred embodiments of the present invention have been described above by way of example only, it will be understood by those skilled in the field that modifications may be made to the disclosed embodiments without departing from the scope of the invention, which is defined by the appended claims.

We claim:

1. An allergen detecting apparatus for detecting the presence of allergen particles in environmental air, comprising:
   a light source for directing a light beam in a light path through a sample of environmental air, whereby portions of the light beam will be scattered by any particles present in the air, said light source having a central optical axis;
   a beam blocking device in the light path for transmitting only light scattered in a predetermined angular range corresponding to a predetermined allergen particle size range, said beam blocking device comprising a circular beam blocking member of predetermined diameter centered on said optical access wherein said beam blocking member is opaque to light of the wavelength transmitted by said light source, and wherein said predetermined diameter is at least equal to the diameter of the light beam focused onto said beam blocking member, whereby portions of the light beam which are not scattered during passage through the air sample are blocked by said beam blocking member;
   a focusing lens positioned between the light source and air sample for focusing the light beam onto the beam blocking device; and
   a detector position to detect light transmitted by said beam blocking device and producing an output proportional to the amount of light received.

2. The apparatus as claimed in claim 1, wherein said predetermined diameter is greater than the diameter of said focused light beam, and said diameter is sufficient to block light scattered at angles below a predetermined minimum angle.

3. The apparatus as claimed in claim 2, wherein the minimum angle is 4°.

4. The apparatus as claimed in claim 1, wherein the light blocking device further comprises an annular ring of light blocking material centered on said optical axis and surrounding said circular beam blocking member, the annular ring having a predetermined inner diameter greater than the diameter of said circular member for blocking light scattered at angles greater than a predetermined maximum scattering angle.

5. The apparatus as claimed in claim 1, wherein the light source is a light emitting diode.

6. The apparatus as claimed in claim 1, including a control circuit connected to the output of the detector for generating an alarm output signal if the detector output is above a predetermined level.

7. The apparatus as claimed in claim 6, wherein the control circuit includes a pulse counter for counting the number of detector output pulses in a predetermined time interval, and producing said alarm output signal if the number of pulses is above a predetermined level.

8. The apparatus as claimed in claim 7, wherein said predetermined level is adjustable.

9. An allergen detecting apparatus for detecting the presence of allergen particles in environmental air, comprising:
   a light source for directing a light beam through the air passing through a sample of environmental air;
   beam blocking means on the other side of the air sample in the path of the light beam for transmitting light traveling in a predetermined scattering angle range and blocking transmission of all light outside said scattering angle range;
   a detector positioned in the light path after the beam blocking means for detecting light transmitted through the beam blocking means and producing an output signal proportional to the amount of light transmitted; and
   a pulse counter connected to the detector output for counting the number of output pulses from the detector in a selected time period and producing an alarm output if the number of pulses is above a predetermined level.

10. The apparatus as claimed in claim 9, including an alarm indicating device connected to said pulse generator and responsive to said alarm output signal and having an alarm condition indicator which is actuated by said alarm output signal.

11. The apparatus as claimed in claim 9, wherein said predetermined level is adjustable.

12. A method of detecting allergen particles in the air comprising the steps of:
   directing a light beam through a sample of environmental air, whereby portions of the light beam will be scattered by any particle's presence in the air sample and, at least a portion of the light beam will be unscattered;
   focusing the light such that the unscattered portion of the focused light falls onto a blocking member on the opposite side of the air sample, said blocking member having a diameter greater than the diameter of the focused light beam;
   detecting light scattered in a predetermined angular range corresponding to a predetermined allergen particle size range and producing an output pulse for each allergen particle detected; and
   producing an output alarm signal by counting the number of said output pulses within a selected time period, and producing said output alarm signal if said number is above a predetermined level.

13. An allergen detecting apparatus for detecting the presence of allergen particles in environmental air, comprising:
   a light source for directing a light beam in a light path through a sample of environmental air, whereby portions of the light beam will be scattered by any particles present in the air;
   a beam intercepting device positioned in the light path after the air sample for intercepting unscattered and scattered light, the beam intercepting device including beam redirecting means for redirecting any scattered portion of the light beam in a predetermined angular range corresponding to a predetermined allergen particle size range in a predetermined path and beam intercepting means for intercepting at least any unscattered portion of the light beam; and
   a detector positioned in said predetermined path from said redirecting means for detecting light redirected from said beam intercepting device and producing an output proportional to the amount of light received.

14. The apparatus as claimed in claim 13, wherein the beam intercepting device comprises a concave mirror.

15. The apparatus as claimed in claim 14, wherein the concave mirror has a central opening of predetermined dimensions comprising said beam intercepting means for intercepting any unscattered portion of the light beam and transmitting said unscattered portion through the mirror.

16. The apparatus as claimed in claim 14, wherein the concave mirror has a central blocking portion for blocking at least any unscattered portion of the light beam.

* * * * *